United States Patent [19]
Wentworth et al.

[11] Patent Number: 5,153,519
[45] Date of Patent: Oct. 6, 1992

[54] HIGH VOLTAGE SPARK EXCITATION AND IONIZATION DETECTOR SYSTEM

[76] Inventors: Wayne E. Wentworth, 614 E. Larkspvr Cir., Pearland, Tex. 77584; Stanley D. Stearns, 1201 Archley Dr., Houston, Tex. 77055

[21] Appl. No.: 662,149

[22] Filed: Feb. 28, 1991

[51] Int. Cl.$^5$ .................... G01N 27/62; G01N 27/68
[52] U.S. Cl. .................... 324/464; 324/449; 324/123 R; 73/28.02
[58] Field of Search .............. 324/449, 450, 452, 455, 324/464, 123 R, 71.4, 204; 73/28.02; 436/153; 313/231.41, 231.71; 315/111.01, 111.91; 250/379, 385.2

[56] References Cited
U.S. PATENT DOCUMENTS

| | | | |
|---|---|---|---|
| 3,540,851 | 11/1970 | Vree et al. | 250/83.6 |
| 3,679,973 | 7/1972 | Smith, Jr. et al. | 324/71.4 |
| 4,266,196 | 5/1981 | Kawazoe. | |
| 4,724,394 | 2/1988 | Langer et al. | 324/464 |
| 4,780,284 | 10/1988 | Lovelock | 250/283 |
| 4,789,783 | 12/1988 | Cook | 250/379 |
| 4,851,683 | 7/1989 | Yang et al. | 250/339 |
| 4,866,278 | 9/1989 | Lovelock | 250/306 |
| 4,975,648 | 12/1990 | Lawson et al. | 324/464 |

FOREIGN PATENT DOCUMENTS 0184912 6/1986 European Pat. Off. .
0396291 4/1990 European Pat. Off. .

Primary Examiner—Kenneth A. Wieder
Assistant Examiner—Diep Do
Attorney, Agent, or Firm—Gunn, Lee & Miller

[57] ABSTRACT

A spark detection apparatus is set forth and incorporates a closed chamber for receiving a carrier gas flowing therethrough between inlets and outlets, and the carrier gas is exposed to a pair of electrodes forming a spark across the chamber and through the carrier gas. Compounds of interest interact with the spark. The spark forms a diffusion of electrons or alternately ions during the spark distributed thereafter. The chamber includes a detector electrode spaced from the spark. High mobility particles (primarily electrons) are observed almost instantaneously with the spark while low mobility ionic particles diffuse more slowly after the termination of the spark. Using an inert carrier gas, high energy metastable molecules are dispersed and give up energy over time after the spark. The output is obtained from the electrode during, immediately after, or after a long delay relative to the spark. Another alternate output is obtained from the observed spectra during the spark and after the spark.

42 Claims, 2 Drawing Sheets

HIGH VOLTAGE SPARK EXCITATION AND IONIZATION DETECTOR SYSTEM

BACKGROUND OF THE DISCLOSURE

The present disclosure involves the creation of several charged species by a pulsed DC spark discharge acting on a carrier gas, typically helium, which utilizes the charged species to classify and/or quantify compounds in the carrier. This detector is connected with upstream or downstream devices such as a sample source, gas chromatograph (GC) column spectrum analyzers, etc. Understanding of various test procedures will illuminate use of the described apparatus and can be gained from review of the apparatus and its mode of operation in a system. A sample to be evaluated is first loaded along with a carrier gas into a system column. The sample passes through this device, a pulsed, high voltage, direct current (DC) spark discharge which forms selected charged or energized species as will be described. As a result of the spark discharge, several types of detection systems are initiated by this detector. For instance, the very short DC spark creates a readily available thermalized electron flux which can be used in a detection system. In an alternate mode of operation, the spark also creates a more slowly diffused flux of metastable helium atoms which drift toward selected electrodes at a controlled rate. The helium atoms will react with molecules of the sample to surrender the excess energy from the excited state to cause sample molecule ionization which, as a secondary reaction, can be measured by a detection system. Another aspect involves transitory photoionization of gas into positive and negative charged particles normally recombining at high speed. If a selected sweep pulse voltage is applied, the recombination is prevented to furnish a current signal indicative of gas contents.

The preferred form this system features a pulsed DC spark discharge in the carrier gas flow which is followed by a rather slow metastable carrier gas dispersion and secondary reaction, which is slow in contrast with the practically instantaneous electron initiated interaction. The DC spark discharge therefore enables two different detection mechanisms, as will be explained, so that variations in detection electrode geometry and pulse timing can obtain different types of responses. One system uses the highly mobile electron flux while an alternate system relies on the metastable carrier gas molecular energy interchange occurring well after the electron flux.

In addition to the particle interaction initiated in the spark manifest in two different aspects, there are also two spectral emissions created by the DC spark, one occurring during the spark and the other occurring later. In the spark gap, the electron discharge creates a first observable spectrum which can be observed by viewing the spark region. Geometry of the spark is sharply defined, narrowly confined, and repetitively located for observation and spectral analysis. This analysis enables detection of the atomic species in the gap. While this first spectrum is extinguished at the end of the spark, a second spectral analysis is enabled by the subsequent decay of metastable helium atoms giving up their excess energy by ionizing molecules of the sample. This interchange occurs as the energized helium atoms diffuse from the spark gap in the test chamber and with the sample molecules. Dependent on relative concentrations, diffusion and flow rates, the sample molecules are ionized to emit energy characteristic of the species. This delayed emission is useful in species identification when timely observed, and therefore a different mode of observation is used to capture data from this emission. This difference in operation derives primarily from delayed occurrence and observed at a different time.

The present invention uses to advantage a simple spark gap having a pair of spaced electrodes connected to a current pulse forming system. The pulses are extremely narrow, preferably in the range of a fraction of a microsecond. The DC pulses repetitively form precise, sharp and well defined transgap pulses, liberating the electron flux mentioned and also forming the metastable helium molecules. The spark is fixed in size and relative timing, shape and location. Electrode geometry does not erode with time and electron ejection is uniform. Thus, the spark is fixed for observation by spectral analysis. Structurally, this enables a very simple chamber to deploy a pair of opposing, spaced electrodes in a cavity or perhaps 10 to 100 microliters volume with gas flow inlet and outlet ports. In a representative system, a chemical sample is mixed with a carrier gas. The sample is prepared for testing by classification, identification or quantification using the detector. An exemplary system achieves separation as a result of differences in travel time through a GC column input to the detector. As is well known, the GC column is packed with a stationary phase material so that the carrier gas and the compounds making up the sample are eluted from the GC column. As a generalization, the mobile phase (a flowing gas or liquid) is delivered by the GC column into this detector for detection of the separated chemical constituents making up the sample.

The detector is operated periodically to test each of the sample constituent compounds passing through the detector. One type of detector used in the past has been the electron capture detector (ECD). The present disclosure sets out an alternate form of ECD detector used in conjunction with a GC column which forms an output signal of substantial sensitivity. The present system features an ECD with a DC pulsed, high voltage spark discharge. As noted at column 2 of U.S. Pat. No. 4,851,683, DC discharges have been known, but they generally have had inhomogenous excitation characteristics and are unstable because of electrode heating and erosion. U.S. Pat. No. 4,509,855 is a DC atmospheric pressure helium plasma emission spectrometer. Additional devices are shown in U.S. Pat. No. 4,866,278. The present apparatus sets forth a DC pulsed, high voltage, spark discharge source which provides a repetitive uniform spark. The spark has a duration which is only a fraction of a microsecond. It would appear that an acceptable spark duration is a part of a microsecond. Moreover, the spark gap is structurally fixed to have a finite width for discharge of the spark created by accumulating energy in a reactive circuit such as a coil and capacitor tank circuit and dumping the energy across the spark gap after charging. Preferably, a nonringing current is applied.

This detector in a representative form includes a means for forming a stabilized spark gap so that the spark and resultant charged particle population are uniform in contrast with the problems referenced in the two mentioned patents. Accordingly, the carrier fluid (e.g., carrier flow from the GC column) is directed as a gas flow through appropriate tubing into a spark chamber. The gas is forced to flow in the spark chamber past a pair of electrodes which are arranged to direct the spark transverse to the gas flow. In a first mode of operation, a flux of electrons is obtained. These electrons are quickly dissipated during the spark interval even though spark duration is only a fraction of a microsecond. The number of electrons available can be measured by means of an electrometer connected to electrodes spaced remotely from the spark gap. The circuitry connected with a terminal spaced from the spark gap detects and measures the electron flux resulting from the spark discharge. In this instance, the spark gas works as an ECD. There is, however, an alternate charged particle flux which is delayed after the spark discharge which uses an ionization mode. This involves a delay of up to about 100 or even 200 microseconds after the spark discharge creates ionized molecules which are dispersed at a slower rate compared with the more mobile electron dispersal. The spark disperses highly energized electrons during the spark and also creates a second and slower dispersion of metastable carrier gas molecules (preferably helium) after the spark. Charged particle dispersal of the first form is, as a practical matter, instantaneous while metastable helium dispersal is time delayed. The two types of dispersion are readily identified because they involve different types of particles. The dispersal of metastable helium atoms, with an elevated energy state of about twenty or more eV, can be observed at a distance from the spark gap so that sample compound concentration (a scale factor) in the chamber is measured. The metastable helium concentration is useful because it enables this delayed reaction. Thus, the metastable helium atom reacts with the sample molecules input with the carrier flow. The high energy in the helium ionizes the sample molecules, creating a measurable current in the chamber.

Building on the last possibility, metastable helium molecules may combine with a trace constituent such as a dopant supplied with the carrier (helium) gas. One such dopant is nitrogen which, in reaction with the metastable helium, forms nitrogen ions. That causes liberation of electrons which again, because of different mobility, dissipate more readily. Before the electrons recombine with the ionized nitrogen molecules, they will react with the compounds making up the sample flowing through the detector. A connected electrode and electrometer will measure electron capture from the dopant involvement to define an electron capture detector.

Another alternate form of apparatus involves observation of the spectrum emitted in the spark gap. This involves the conversion of the constituents to elevated energy states where emissions occur at characteristic frequencies, and such frequencies can be observed and measured. This typically involves a spectrum analyzer such as a spectrometer which observes one or more atomic or molecular emission lines in selected regions of the spectrum. Spectral line observation varies with the time and location relative to the spark discharge. Regarding time, the observed spectrum is different during and after the spark discharge. Regarding location, the reaction is different in the spark or elsewhere in the chamber. The present apparatus is therefore summarized as a pulsed DC spark discharge where the spark discharge reacts with a carrier gas (preferably helium) and compounds from a sample. In this spark, charged particles are created, the particles being either disassociated electrons, an ionized carrier gas, ionized dopant gas, or highly energized helium atoms in a metastable form. Depending on the timing of measurements, the particular ionized particles and measurement voltages applied, the device can be operated in an ionization mode, or electron capture mode. Molecules of a compound separated by chromatographic separation or other input devices can be quantified. The device also emits characteristic spectral lines depending on the nature and timing of the emission. Moreover, by selection of the carrier gas, the addition of a selected dopant with the gas flow, control of pulsing of the spark gap forming the charged particles, timed operation of measurement electrodes nearby, and adjustment of scale factors, it is possible to operate in several modes. In addition to this, precisely defined spectral lines can be observed.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
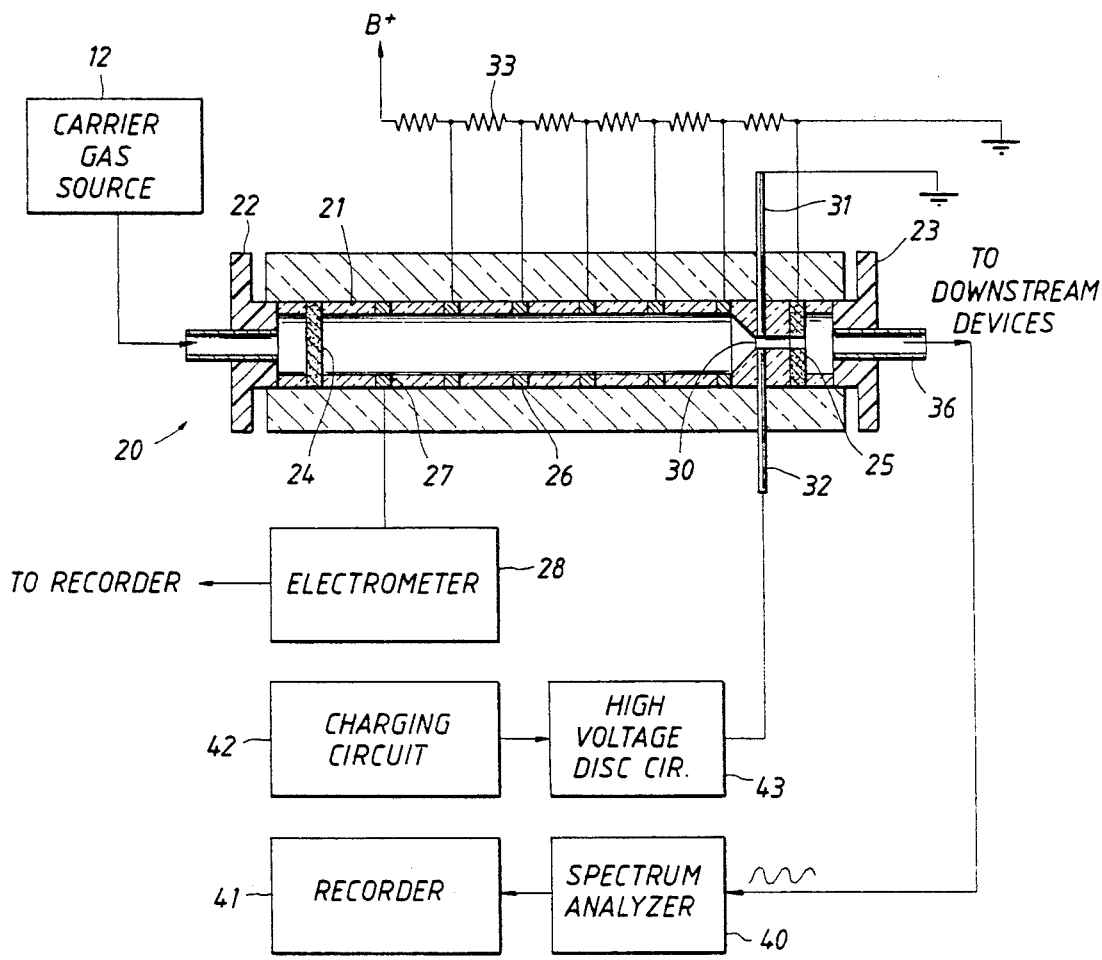
FIG. 1 is a schematic block diagram of the detector of this disclosure showing a pair of fixed electrodes in a spark gap for pulsed DC discharge in a flowing stream to form charged particles.

The present disclosure is directed to an ionization detector system connected with upstream and downstream equipment. The cooperative equipment defines one context for ease of explanation so that a thorough discussion of the spark detector system will provide the necessary explanation. This is a detector system devoid of radioactive apparatus and hence can be used in circumstances where radioactive materials are limited. Heretofore, it has been common to operate electron capture devices with radioactive sources, the most common sources being tritium or nickel 63. Typically, these emit beta particles which trigger operation of the electron capture detector or perhaps helium ionization detectors. In this particular instance, a non-radioactive device is thereby provided. Going now to FIG. 1 of the drawings, the numeral 20 identifies a detector system of the present disclosure. It will be described proceeding from the input in the fashion of a flow chart, and after that, certain features of the high voltage DC powered pulsed spark discharge system will be discussed, and its interaction with various types of detector systems including charge measuring devices and spectrum analyzers will also be set forth. Certain equations will be given which are believed to correctly describe the nature of the particles of the process. At this stage, the detector will be described solely with a carrier gas, and its operation dates will be given with various inputs.

The present detection system utilizes a carrier gas source 12 connected to the detector with an input valve (not shown). The source provides a carrier gas flow and a sample will be discussed later; there is a constant flow delivered into and through the detector at a controlled pressure and flow rate. Briefly, a carrier gas is supplied in a steady flow rate and pressure. Representative sample compounds may include various and sundry halocarbons and other organics which are carried with the flowing carrier gas. For representative purposes, a specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. It is preferable that the sample AB be delivered with helium as the carrier gas. While several gases can be used, the preferred carrier gas is helium. Purity will be discussed below. The gas flow is directed to an inlet opening 18 of the plasma detector 20. This detector includes a closed elongate tube 21 which has an end cap 22 opposite a similar end cap 23. They are both provided with ports for flow through the detector. The central tube is axially hollow and has a uniform diameter throughout the length except at the spark electrodes as will be mentioned.

The detector 20 is formed of an insulating material. The tube can be glass or the like. The flow is through transverse disc 24 formed of sintered metal to provide a serpentine inlet pathway and also provide a barrier to charged particle migration further to the left. At spaced locations, there are exposed metal rings such as the rings 25. One of the rings is more remote while other rings are serially closer. The rings are serially arranged downstream from the inlet end. There are several intermediate rings 26 which are tied to various resistors for voltage taps as will be explained. There is also a ring 27 which is connected to an electrometer 28. The electrometer can be connected elsewhere along the length of the passage; it is connected to a selected or particular terminal which is exposed to charged particle population within the tube to detect current flow resulting from charged particle migration.

The number 30 identifies a spark gap which is defined by two round and equal diameter rods. They have a finite width which measures a fraction of a millimeter up to about two millimeters. The tips are cut flush and are made free of burrs to form opposing, parallel faces. The two tips are held by a support ring which can be integral with the support structure. The two tips are aligned opposite one another so that they are precisely diametrically opposite each other within the passage and thus define the spark gap 30. They are supported by a surrounding structure of non-conductive material such as plastic, ceramic or the like. All flowing gases must pass between the two tips. This passage is ideally a small diameter passage, perhaps having a diameter of about one millimeter, and it can be less; the two electrodes are preferably spaced from one another by something between 0.5 and 1.5 millimeters. They can be spaced slightly farther apart if desired. The two electrode tips are flush and do not protrude into the cylindrical passage.

The two electrodes are identified by the numerals 31 and 32, and the electrode 31 is grounded. The electrode 32 is provided with a high voltage pulse as will be described. A very short pulse is preferred. The caps 22 and 23 at the two ends of the structure seal against the intrusion of external air so that the only gases flowing through the system are the carrier gas and the compound AB mixed with the carrier gas and which interact with the spark as individual compounds pass through the spark discharge.

The several electrodes 26 are connected to a voltage ladder which is made up of several series connected resistors 33. B+ is provided for this system. It can be pulsed off and on, being furnished by a B+ supply 34 subject to control of the timer 16. The voltage can be positive or negative depending on charged particle detection. Moreover, the voltage applied to the rings is proportioned by the resistors 33. To this end, one end of the resistor ladder is grounded and the opposite end is connected at B+, and that voltage is switched off and on as will be described in a timed fashion relative to the pulse formed between the electrodes 31 and 32. The flowing carrier gas including the compound AB is directed through the DC spark generator 20 and flows through the outlet port 36. The port 36 is aligned with the port 18 at the opposite end, and the port 36 is particularly directed at the spark gap 30 between the two electrodes. This serves as an observation port to enable optical inspection of the gap during the spark. This enables photons of light emitted by the spark gap to impinge on an external spectrum analyzer 40 which is positioned opposite the outlet opening 36. In turn, the analyzer connects with a recorder 41 for recording the data as a function of time. The system also includes a charging circuit 42 which connects with a high voltage discharge circuit 43 to provide a timed pulse for firing, that is, a pulse which is timed to initiate formation of various charged particles where representative particle reactions will be detailed later.

Figure 3:
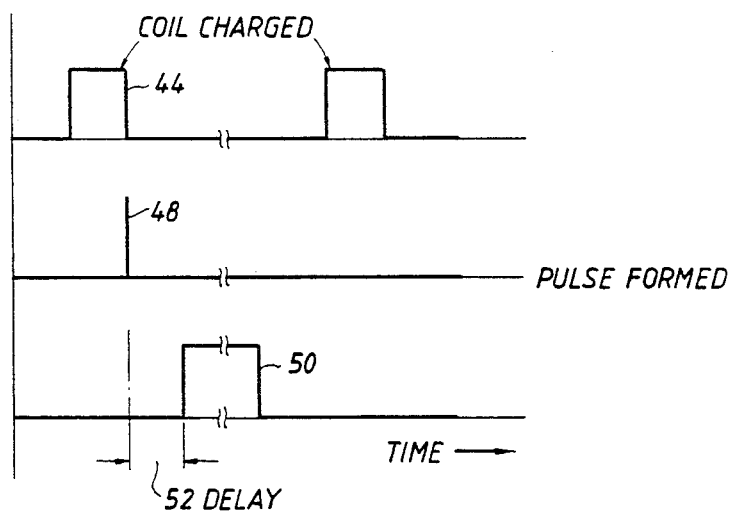
FIG. 3 is a timing chart showing the timed relationship of operations of circuitry shown in FIG. 2 of the drawings.

Going now to FIG. 3 of the drawings, several curves are shown which are a function of time. The top curve shows a charging current in the pulse 44. It forms the necessary charge for operation of the high voltage discharge circuit 43. That circuit forms an output 48 which pulse flows for a relatively short instant. There is a detection interval which is delayed by a specified time 52, and then a detection pulse is formed at 50. Representative values of these pulse durations and spacing will be given.

The spark discharge generator 20 is sealed to exclude external air. It therefore is exposed to a flow of AB and helium in the preferred embodiment. A trace element dopant may optionally be mixed with the carrier gas. A suitable dopant material is $N_2$ which is provided in a controlled quantity, such as one to one thousand parts per million. A typical range for this dopant can be from one part in $10^3$ to one part in $10^9$. The compound AB flows with the carrier helium gas into the chamber and ultimately into the spark gap 30 where the charged particles are formed. The pulse 44 is created for an interval to form the discharge pulse 48. The high voltage discharge circuit 43 forms the discharge pulse 48 which sparks across the gap between the electrodes 31 and 32. Carrier gas in the region of the spark gap 30 is ionized during the spark. The spark is furnished with current flow at a finite voltage; the spark cannot fluctuate because the only mode of current flow is by means of a spark across the gap. The voltage necessary to achieve spark current flow is a function primarily of spacing and tip geometry. The electrode tips are preferably flat cylindrical faces which are fixed at a known distance from one another so that the voltage necessary to create the spark is fairly stable. Moreover, ambient pressure is maintained in the spark generator 20 so that the voltage does not vary with prevailing pressure. The charging circuit functions like a classic automobile ignition system in that a charging current is provided from a capacitor or the field of a coil and then collapses to provide the current at discharge. When the current flows, it breaks to the peak value required to initiate flow and then drops substantially to zero, thereby discharging the circuitry that had been previously charged. Preferably, ringing in the supply circuit is suppressed. Moreover, the discharge occurs near the trailing end of the pulse 44 so that the pulse 44 can be used to indicate the time of discharge. It should be noted that the pulse 44 can have a substantial width, ranging from a few microseconds up to many microseconds, at most perhaps 100 to 200 microseconds. Peak amplitude of the discharge pulse 48 is substantially determined by the geometry and spacing of the electrodes 31 and 32.

When current flows through the gap between electrodes 31 and 32, particle excitation occurs. Among other things, elemental helium atoms will be energized when raised to the metastable state where they hold enhanced energy. The metastable helium ultimately diffuses from the spark gap in the chamber in a fashion to be described. While a metastable helium may have an elevated energy level of about twenty eV, it has a fairly long half life, but because of its size, relatively speaking, it diffuses somewhat slowly. The metastable helium atoms will diffuse at some rate in all possible directions. This diffusion rate and range can be enhanced depending on housing geometry and detector electrode geometry, placement and voltage. Moreover, when the pulse 40 occurs, there is a substantial electron discharge into the carrier gas atmosphere from the gap, and the electron concentration in the immediate vicinity of the spark gap is quite high. That is, an extraordinary number of electrons is emitted and distributed into the immediate atmosphere. These electrons drift the length of the generator 20 rapidly. The diffused electrons can be observed throughout the generator 20 and can be measured by the electrometer 28 output.

There are several equations which are helpful to describe the relatively simple sequence of events occurring in the plasma tube. Recall again that flow is from the inlet port 18 to the outlet port 36. Even though the flow is in that direction, diffusion of the charged particles to the left of the spark gap 30 can be initiated and controlled by choice of polarity and potential on the detector electrodes. Indeed, the mobility of electrons is substantially instantaneous to the extent that electrometer response can be observed rapidly even though the spark has a width of less than one microsecond, perhaps a width of only 10 to 250 nanoseconds. The nearly instantaneous diffusion of electrons primarily results from their extreme mobility in comparison with larger charged particles, meaning the metastable heliums. Regarding the spark, the voltage across the terminals is typically several thousand volts prior to current flow; once current flow begins, the voltage across the terminals rapidly changes as current flow changes from the initial zero value toward the peak current and then decays. The pulse duration is relatively easy to define at the start of the pulse but it may be difficult to define at the end of the pulse. There are two reasons for this; the first reason is that the power supply may ring and provide post pulse current reversals. This is preferably suppressed by incorporating means to damp the ringing. A second reason is more subtle, and relates to the ionized particles between the electrodes at the end of the pulse. The resistance across the electrodes may be very low, perhaps so small that it permits current flow even when the voltage is nil. One may postulate that the ionized particles between the electrodes are so instantaneously dynamic that current flow can be observed at the facing electrodes even though the power supply, at that instant, provides no voltage.

Figure 2:
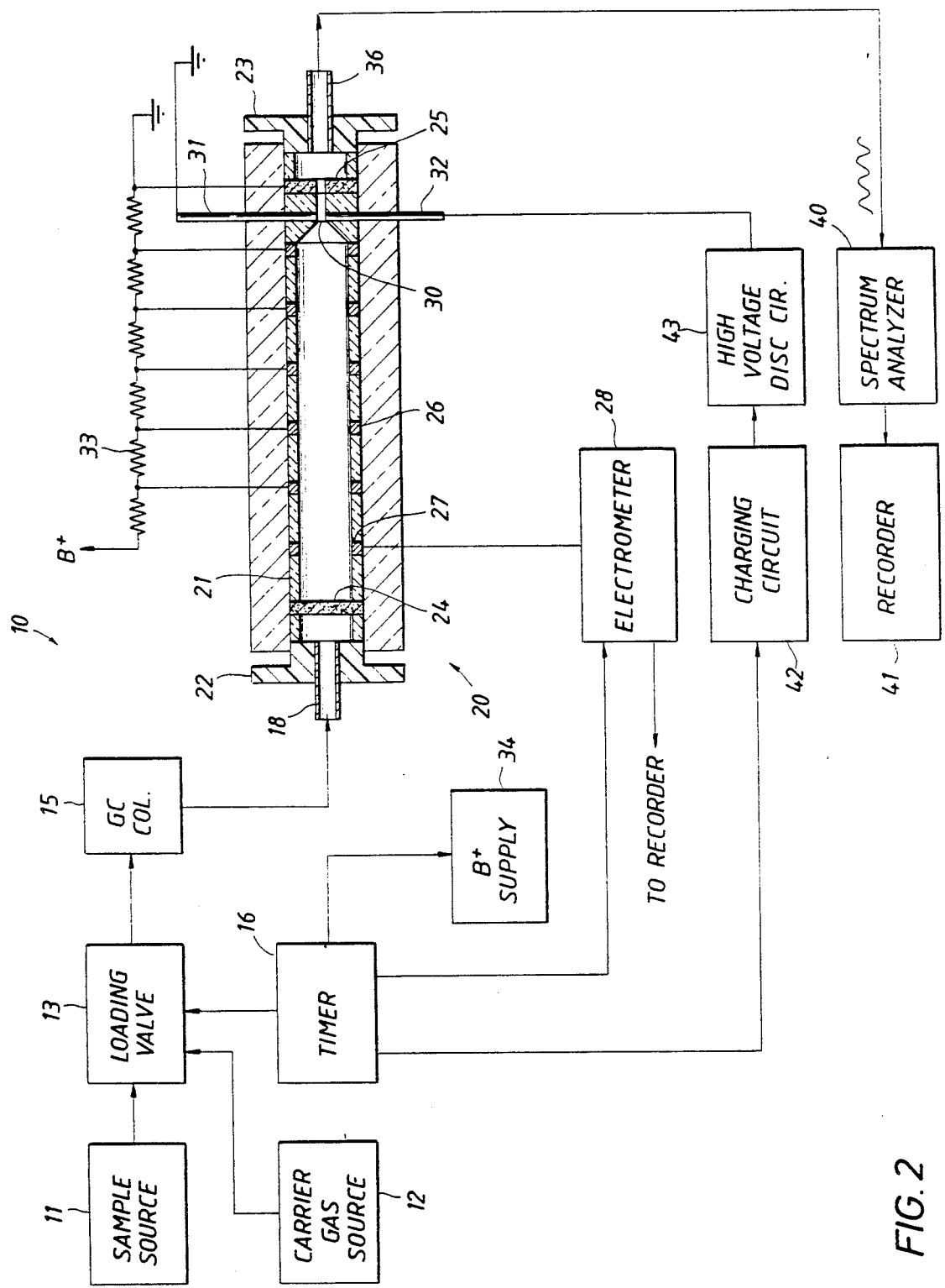
FIG. 2 is a schematic block diagram of a system for testing an unknown sample where the sample and a carrier gas are input through a GC column and the elute therefrom is directed into a discharge tube having a number of electrodes for charged particle capture and also having a pair of fixed electrodes for pulsed DC discharge in the flowing stream, and further including a spectrum analyzer observing the light emitted on spark discharge.

FIG. 2. shows the present detector in a representative GC system which utilizes a sample source 11 and a carrier gas source 12 which are both connected with a loading valve 13. They provide a carrier gas flow at a constant flow delivered at a controlled pressure and flow rate to a GC column 15. There is a system timer 16 which controls the operation of certain components as will be set forth. Briefly, a carrier gas is supplied in a steady flow for the GC column. Representative compounds include various and sundry halocarbons and other organics which are supplied with the flowing carrier gas through the loading valve 13 to the GC column 15. As before, a specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. The discharge of the GC column 15 is directed to an inlet opening 18 of the plasma detector 20.

DESCRIPTION OF CHARGED PARTICLES AND THEIR REACTIONS

There are several results which occur as a result of the spark discharge through the spark gap. For one, the pulsed spark discharge causes immediate energization of molecules (atoms of helium) in the elute. The mechanism apparently involves collision of the high energy electrons in the spark gap with the carrier molecules. In addition to that, molecules (again atoms of helium) in the elute may subsequently emit radiation in a unique spectral distribution characteristic of the excited species and hence form characteristic emission spectra. The several processes occurring during the spark discharge can be summarized by the following five different reactions:

$$e^- + AB \rightarrow AB^+ + e^- \quad (1)$$

$$e^- + AB \rightarrow A + B^+ + e^- \quad (2)$$

$$e^- + AB \rightarrow AB^* + e^- \text{ where } AB^* \rightarrow AB + h\nu \quad (3)$$

$$e^- + AB \rightarrow A + B^* + e^- \text{ where } B^* \rightarrow B + h\nu \quad (4)$$

$$e^- + AB \rightarrow (AB^+)^* + e^- \text{ where } (AB^+)^* \rightarrow AB^+ + h\nu \quad (5)$$

Another reaction which does occur as a result of the pulsed high voltage spark discharge is the conversion of helium into high energy metastable atoms having an energy of about nineteen eV. This reaction is given in Equation 6:

$$e^- + He \rightarrow He^* + e^- \tag{6}$$

In the foregoing, He* represents the metastable helium atom just as the * above in Equations 3, 4 and 5 represents an enhanced energy level for the particular molecule represented by the symbol AB. In the case of metastable helium, it has a relatively long life, measured perhaps to 100 seconds, and the enhanced energy state has sufficient energy to cause subsequent reactions. Equations 7, 8, 9 and 10 describe selected reactions which can occur involving the metastable helium. As will be understood, the metastable helium extends the duration of the process long after the spark discharge is terminated. In fact, the metastable duration can be hundreds of milliseconds while the spark duration might be only a few nanoseconds. The equations below describe various ionization or excitation results from the metastable helium which results are quite different from those initially caused by the high voltage spark discharge set forth in Equations 1-5 above. Accordingly, Equations 7-10 generally summarize the following reactions resulting from the metastable helium.

$$He^* + AB \rightarrow AB^- + e^- + He \tag{7}$$

$$He^* + AB \rightarrow A + B^- + e^- + He \tag{8}$$

$$He^* + AB \rightarrow AB^* + He \text{ where } AB^* \rightarrow AB + h\nu \tag{9}$$

$$He^* + AB \rightarrow A + B^* + He \text{ where } B^* \rightarrow B + h\nu \tag{10}$$

Equations 3, 4, 5, 9 and 10 all describe reactions which form specific and characteristic emission spectra, thereby providing a characteristic signal which enables analysis of the emission source. However, one set of spectra will be emitted during the spark and another set of spectra will be emitted after the spark in view of the longer decay times involved, for example, in the last four equations above.

Building on this, a sequence of operation will be described. This involves pulsing the high voltage supply to obtain the appropriate high speed pulse so that certain phenomena occur during the spark, and other phenomena occur after the spark, enabling analysis of different emission spectra at different times relative to the spark and its duration. Discussion of these timing factors can also be tied to a discussion of scaling factors relating to particular voltages.

Measurement of a particular charge species is normally made upstream of the spark gap 30 where the electrometer is located. Carrier gas flow from left to right at a specified rate is a scale factor which relates to system sensitivity. Moreover, system sensitivity is controlled by adjustment of the B+ voltage (positive or negative) applied in the chamber 20. Also, sensitivity is impacted by the choice of the particular electrode 26 and the spacing from the spark gap. Timing is another important scale factor which is exemplified in FIG. 3 in the delay 52 which occurs after the pulse 48 but before enabling the B+ with the waveform 50. Consider a typical example. When detecting ions larger than electrons, the detection pulse is applied for a longer interval of time to detect ionic dispersion from the spark gap. Thus, the compound AB forms ionic particles in the spark gap 30 which are measured by periodically pulsing the B+ for detection. Assume that a pulse 44 of twenty microseconds in width causes firing, the spark being the pulse 48 which has a width of substantially less than one microsecond, perhaps a width in the range of 10 to 200 nanoseconds. The time delay 52 can be anywhere from 20 to 200 microseconds which enables ions to form after the spark and migrate to the left in FIG. 1 so that the charged particles (less mobile than electrons) are in the vicinity of the appropriate electrodes. This movement is influenced by the geometry and voltage of the several electrodes. In this example, the electrode 27 is controlled by the timer 16 to switch on coextensive with the pulse 50 which is applied to the B+. The electric field formed by the various electrodes 26 controls charged particle dispersion toward the electrode 27. The electrometer 28 measures the impingement of electrons at the terminal 27 and forms an output signal. This can be repeated in cyclical fashion. For instance, the pulse 48 can be repeated with a pulse spacing of one millisecond. In contrast with the flow rate and relative time duration in which a compound AB is in the system, this assures that the peak will be sampled many times. For instance, assume that the GC column elute discharges the AB compound over a two second interval. Assume further that the next compound is discharged over a four second interval. Assuming the first elute transit time through the detector 20 is equal to the duration of the peak, over 2,000 samples for that peak will be obtained. The 2,000 data points thus encode the data to assure that proper measurement is obtained and is output for the recorder 41.

As will be observed in the foregoing, the measured charged particles (whether small, highly mobile electrons or larger and less mobile ions) can be timed or gated so that detection of one can occur during the spark and for a very short duration thereafter, or alternately, long after the spark is terminated. Because of the differences that result during the spark versus the reactions occurring after the spark, the phenomena represented by Equations 1-10 above are different and can be distinguished by observation either of the concentration of electrons or ionized particles or by observation of the different emission spectra. Moreover, the emission spectra is different from different regions within the detector. If, for instance, the emission spectra is observed during the spark in the spark gap, the spectra is different from the spectra observed away from the spark gap, as for example, observation of the spectra upstream of the spark gap.

One valuable benefit of the present apparatus is use of the pulsed high voltage spark discharge as a ionization detector devoid of radioactive sources. This can be done either by using the ionization during the discharge or the ionization after the discharge resulting from the metastable helium atoms. The different ionization initiated responses are thus quite different, and they can be used as a qualitative test of suspected compounds. So to speak, the pulsed system serves as two separate detectors testing the carrier and compound AB repetitively, providing two output signals which can be separated and yet which correlate to enhance peak analysis.

If desired, the pulsed high voltage spark discharge system can be used in an electron capture detector devoid of a radioactive source. The helium gas can be provided with a dopant gas; the preferred dopant is $N_2$ which creates a relatively high standing current as a result of ionization of the $N_2$. In the event the elute molecule tends to capture electrons, the standing current flow through the device will decrease in proportion to elute molecules introduced into the chamber. Regarding carrier gas choice, the well known inert gases are normally preferred. In some instances, $N_2$ is a good choice.

Connected upstream and downstream, devices are important in use of the detector. For instance, in a manufacturing plant, a single compound AB can be tested repetitively. A variety of unknown compounds can be tested with GC separation as mentioned. The present detector can be connected by any suitable supply system to enable testing and quantification of one or more compounds. The detector output is alternately furnished by the current flow from the electrode 27, or is optically determined by the spectrum analyzer. In both instances, the data is potentially different during the pulse and immediately thereafter in contrast with waiting a long interval after the spark. This enables an entirely different measurement to be obtained.

While the foregoing is directed to the preferred embodiments, the scope thereof is determined by the claims which follow.

What is claimed is:

1. A charged particle detector comprising:
   (a) a closed chamber having a gas flow inlet and spaced outlet to enable gas flow therethrough;
   (b) spaced electrodes forming a spark responsive to periodically pulsed DC current flow sufficient to enable an electrical arc to be formed between said electrodes defining the spark thereacross, said electrodes being positioned in said chamber to form a spark gap across gas flow through said chamber;
   (c) a spaced detector electrode in said chamber for collection of charged particles formed as a result of the spark across the gap wherein the charged particles move toward said detector electrode impinging thereon to enable a current to be formed indicative of charged particle concentration in said chamber;
   (d) a voltage source connected to said detector electrode to provide a controlled voltage thereto for enabling said detector for charged particle impingement; and
   (e) wherein the control voltage in conjunction with a current formed between said spaced electrodes attracts a species of charged particles in said chamber.

2. The apparatus of claim 1 wherein the species is diffused electrons with said chamber.

3. The apparatus of claim 1 wherein said species comprises metastable, inert atoms having an excited energy state which transition to a lower energy state and thereby emit measurable radiation.

4. The apparatus of claim 1 wherein said detector electrode is spaced remotely from said spark forming electrodes and at least one electrode is therebetween connected to a voltage source to control charged particle impingement thereon.

5. The apparatus of claim 4 including multiple electrodes connected to serially increasing voltage levels.

6. The apparatus of claim 1 wherein said spark forming electrodes are periodically pulsed with DC current to form a sustained spark during pulsing wherein the spark forms an incandescent current flow across said gap, and said spark electrodes are flush mounted in a surrounding circular ring of non conductive material to enable gas flow through the spark.

7. The apparatus of claim 6 wherein the spark forming electrodes are flat face circular conductors arranged parallel and facing across said gap.

8. A method of analyzing a sample compound in a carrier gas comprising the steps of:
   (a) flowing the carrier gas and any sample compounds mixed therewith through a chamber for exposure to a periodically pulsed DC current sparks across the chamber;
   (b) forming charged particles as a result of the spark in the chamber wherein the charged particles are formed from the sample, and dispersing the charged particles in the chamber for measurement at a remote point within the chamber; and
   (c) wherein the measurement step occurs at a timed spacing relative to the spark in the chamber.

9. The method of claim 8 wherein the carrier gas is an inert gas capable of being changed to a metastable state by the spark, and further sustains the metastable state for a controlled time interval after the spark.

10. The method of claim 9 wherein the carrier gas is helium and forms metastable helium; and further wherein any sample in the helium carrier provides charged particles for measurement.

11. The method of claim 9 wherein the carrier helium gas includes a controlled trace gas therewith.

12. A method of analyzing a sample compound in a carrier gas comprising the steps of:
   (a) flowing the carrier gas and any sample therewith through a chamber for exposure to a periodically DC current pulsed spark discharge across the chamber; and
   (b) optically observing spark caused emissions from the chamber to analyze the sample flowing through the chamber.

13. The method of claim 12 wherein the observation is made during the spark.

14. The method of claim 13 wherein the spark is DC current flow at a fixed location in the chamber of finite duration and is periodically repeated.

15. The method of claim 12 wherein the observation is made from a region of the chamber not involving the spark.

16. The method of claim 15 wherein the observation is after the spark.

17. The method of claim 16 wherein the carrier gas includes helium, and the observed optical emissions result from emissions of helium energized to a metastable state which emit energy by changing to a lower energy state.

18. The method of claim 16 including the step of dispersing particles from the spark to enable dispersal particle conversion after the spark accompanied by spectra emission.

19. A gas detector for identification and quantitation of sample compounds, comprising:
   (a) an elongated chamber having a chamber inlet at one end and an outlet at the other end, and a gas flow path between said inlet and outlet ends;
   (b) means for flowing carrier gas supply for said chamber;
   (c) means for introducing sample gas into said chamber;
   (d) two electrodes spaced apart and located to produce short repeated high voltage pulsed DC current sparks within said chamber and across said gas flow path and wherein spark duration minimizes electrode erosion and permits observation of phenomena occurring at and between sparks; and
   (e) means responsive to emission of characteristic spectra by sample constituents during the spark and emission of characteristic spectra by sample constituents reacting with metastable excited carrier species between sparks.

20. The apparatus of claim 19 wherein a potential gradient is created between the spark electrodes and a collector electrode in said chamber for the measurement of ionization and electron capture phenomena.

21. The apparatus of claim 19 wherein a window is provided in said chamber to observe spectral emission occurring at and between sparks.

22. The apparatus of claim 21 wherein a series of electrodes provide a focusing electrical gradient to measure the mobility at ions formed by the spark.

23. The apparatus of claim 19 wherein ultrapure inert gas is a carrier gas to measure sample by photoionization, metastable ionization, and direct ionization.

24. The apparatus of claim 23 wherein a dopant is added to the carrier gas to provide a source of thermalized electrons to measure electron capture.

25. A gas detector for identification and quantitation of sample compounds, comprising:
(a) an elongated chamber having a chamber inlet at one end and an outlet at the other end, and a gas flow path between said inlet and outlet ends;
(b) means for flowing carrier gas supply for said chamber;
(c) means for introducing sample gas into said chamber;
(d) two electrodes spaced apart and located to produce short repeated high voltage pulsed DC current sparks within said chamber and across said gas flow path and wherein spark duration minimizes electrode erosion and permits observation of phenomena occurring at and between sparks; and
(e) wherein ions are produced by the spark and by excited metastable species of the carrier gas.

26. The apparatus of claim 25 wherein a potential gradient is created between the spark electrodes and a collector electrode in said chamber for the measurement of ionization and electron capture phenomena.

27. The apparatus of claim 26 wherein a series of electrodes provide a focusing electrical gradient to measure the mobility at ions formed by the spark.

28. The apparatus of claim 27 wherein a dopant is added to the carrier gas to provide a source of thermalized electrons to measure electron capture.

29. Detecting apparatus comprising:
(a) an elongate chamber having an inlet at one end and an outlet at its other end, and a gas flow path between said inlet and outlet;
(b) spaced discharge electrodes disposed within said chamber to form an electrical discharge gap between such electrodes in said gas flow path of said chamber;
(c) means for flowing a sample gas with a carrier gas through said gas flow path of said chamber;
(d) means for periodically and repetitively applying DC current discharges across said discharge gap of said spaced electrodes in the path of said sample gas and said carrier gas thereby changing the atomic state of said sample gas and carrier gas; and
(e) means for measuring a characteristic of the changed atomic state of said sample gas.

30. The apparatus of claim 29 wherein said electrical discharges are of a duration of from about about 10 microseconds to about 50 microseconds in length with a time period between pulses of about 125 microseconds to about 500 microseconds.

31. The apparatus of claim 29 wherein said elongate chamber includes a portion of restricted diameter, and wherein said spaced discharge electrodes are placed apart from each other in said portion of restricted diameter.

32. The apparatus of claim 29 wherein said means for measuring includes a spectrum analyzer means responsive to radiation generated in said flow path of said chamber for identifying atoms and molecules which produce such radiation, timing means for generating a first enabling pulse occurring at substantially the same time interval as said electrical discharge occurs, and means for applying said first enabling pulse to said spectrum analyzer means, whereby said spectrum analyzer means produces an output identification of molecules and atoms which produced radiation during said electrical discharge as a result of their said changed state.

33. The apparatus of claim 32 wherein said means for measuring includes timing means for generating a second enabling pulse delayed in time from the occurrence of said electrical discharge and means for applying said second enabling pulse to said spectrum analyzer means, whereby said spectrum analyzer means produces an output identification of molecules and atoms which produce radiation at a time delayed from said electrical discharge as a result of their changed state.

34. The apparatus of claim 29 wherein said means for measuring a characteristic of said sample gas includes, at least one charge collecting electrode within said chamber which is longitudinally spaced from said discharge electrodes of said chamber, means for establishing an electric field within said chamber for attracting electrons produced in said chamber as a result of said electrical discharges passing through said carrier gas and said sample gas, electrometer means connected to said charge collecting electrode for measuring charge collected per unit time on said charge collecting electrode, and means for recording said charge collected per unit time as a function of time, as an indicator of the ratio of said sample gas to said carrier gas.

35. The apparatus of claim 30 wherein said means for measuring a characteristic of said sample gas includes at least one charge collecting electrode within said chamber which is longitudinally spaced from said discharge electrodes of said chamber, means for establishing an electric field within said chamber for attracting electrons produced in said chamber as a result of said electrical discharges passing through said carrier gas and said sample gas, electrometer means connected to said charge collecting electrode for measuring current on said charge collecting electrode, and timing means for enabling said electrometer means substantially during the time of said electrical discharges to measure a first current and for enabling said electrometer during time intervals between said electrical discharges to measure a second current, whereby a ratio of said first current of said second current is an indicator of a characteristic of said sample gas.

36. The apparatus of claim 30 wherein said means for measuring a characteristic of said sample gas includes at least one charge collecting electrode within said chamber which is longitudinally spaced from said discharge electrodes of said chamber, means for establishing an electric field within said chamber for attracting electrons produced in said chamber as a result of said electrical discharges passing through said carrier gas and said sample gas, electrometer means connected to said charge collecting electrode for measuring current on said charge collecting electrode, means for establishing gas flow during a first time through said chamber which includes solely said carrier gas and nitrogen gas, and means for establishing gas flow during a second time through said chamber which includes said carrier gas, said nitrogen gas and a sample gas, whereby a difference in current measured by said electrometer means during said first time and current measured by said electrometer means during said second time is an indicator of said sample gas.

37. A method of measuring a characteristic of a gas sample comprising the steps of:
 (a) providing an elongate chamber having an inlet at one end and an outlet at its other end and a gas flow path between said inlet and outlet, with spaced discharge electrodes disposed within said chamber to form an electrical discharge gap between such electrodes in said gas flow path of said chamber;
 (b) flowing a sample gas with a carrier gas through said gas flow path of said chamber;
 (c) repetitively applying pulsed DC current discharges across said discharge gap in the path of said sample gas and said carrier gas thereby changing the atomic state of said sample gas; and
 (d) measuring a characteristic of the charged atomic state of said sample gas.

38. The method of claim 37 wherein said measuring step includes the sub-steps of applying radiation generated in said flow path to a spectrum analyzer during substantially the same time interval as said electrical discharges occur, and recording the output of said spectrum analyzer thereby enabling identification of atoms and molecules which produce such radiation.

39. The method of claim 37 wherein said measuring step includes the sub-steps of applying radiation generated in said flow path to a spectrum analyzer during time intervals between said electrical discharges, and recording the output of said spectrum analyzer thereby enabling identification of atoms and molecules which produce such radiation.

40. The method of claim 37 wherein said measuring step comprises the steps of providing a charge collecting electrode within said chamber which is longitudinally spaced from said discharge electrodes of said chamber, providing an electric field within said chamber for attracting electrons produced in said chamber as a result of said electrical discharges passing through said carrier gas and said sample gas, measuring charge attracted to said charge collecting electrode as a function of time, and recording said charge collected as a function of time as an indicator of said sample gas in said carrier gas.

41. The method of claim 37 wherein said measuring step comprises the steps of providing a charge collecting electrode within said chamber which is longitudinally spaced from said discharge electrodes of said chamber, providing an electric field within said chamber for attracting electrons produced in said chamber as a result of said electrical discharges passing through said carrier gas and said sample gas, measuring charge attracted to said charge collecting electrode substantially during the time of said periodic electrical discharges and indicating the measured current, measuring charge attracted to said charge collecting electrode during the time between said periodic electrical discharges and indicating the measured current, as an indicator of a characteristic of said sample gas in said carrier gas.

42. A method of identifying a gas sample comprising the steps of providing an elongated chamber having an inlet at one end and an outlet at its other end and a gas flow path between said inlet and outlet, with spaced discharge electrodes disposed within said chamber to form an electrical discharge gap between such electrodes in said gas flow path of said chamber, providing a charge collecting electrode within said chamber which is longitudinally spaced from said discharge electrodes of said chamber, providing an electric field within said chamber for attracting electrons produced in said chamber as a result of periodically pulsed DC current electrical discharges passing through said carrier gas and said sample gas, flowing a carrier gas doped with nitrogen gas through said gas flow path of said chamber and measuring charge attracted to said charge collecting electrode as a function of time, flowing said carrier gas doped with nitrogen gas with said sample gas through said gas flow path of said chamber and measuring charge attracted to said charge collecting electrode as a function of time, so that the difference, in measured levels is an indicator of the identification of said sample gas.

* * * * *